(12) United States Patent
Suer et al.

(10) Patent No.: US 7,566,545 B2
(45) Date of Patent: Jul. 28, 2009

(54) METHOD FOR PRODUCING A NUCLEOSOME PREPARATION AND USE THEREOF IN IN VITRO DIAGNOSIS OF DISSEMINATED LUPUS ERYTHEMATOSUS (DLE)

(75) Inventors: Waltraud Suer, Buchholz (DE); Cornelia Dähnrich, Gross Grönau (DE); Wolfgang Schlumberger, Gross Grönau (DE); Winfried Stöcker, Gross Grönau (DE)

(73) Assignee: Euroimmun Medizinische Labordiagnostika AG, Lubeck (DE)

( * ) Notice: Subject to any disclaimer, the term of this patent is extended or adjusted under 35 U.S.C. 154(b) by 216 days.

(21) Appl. No.: 10/504,569

(22) PCT Filed: Dec. 2, 2002

(86) PCT No.: PCT/EP02/13629

§ 371 (c)(1),
(2), (4) Date: Jun. 20, 2005

(87) PCT Pub. No.: WO03/069337

PCT Pub. Date: Aug. 21, 2003

(65) Prior Publication Data

US 2005/0233322 A1    Oct. 20, 2005

(30) Foreign Application Priority Data

Feb. 15, 2002   (DE) ................ 102 07 735

(51) Int. Cl.
*G01N 33/53* (2006.01)
*G01N 33/543* (2006.01)

(52) U.S. Cl. ............. 435/7.21; 435/7.1; 435/7.92; 435/87; 435/91.4; 435/174; 436/501; 436/518; 530/300; 530/350; 536/7.5; 536/23.1

(58) Field of Classification Search ............. 435/7.1, 435/7.21, 7.92, 87, 91.4, 174; 436/501, 518; 530/300, 350; 536/7.5, 23.1
See application file for complete search history.

(56) References Cited

U.S. PATENT DOCUMENTS 4,444,879 A * 4/1984 Foster et al. ............. 435/7.95

OTHER PUBLICATIONS

Olson et al. (Biochemistry, 1983, vol. 22, pp. 3187-3193).*
Maggio (Immunoenzyme technique I, CRC press ä 1980, pp. 186-187).*
Shikama et al. (Molecular and Cellular Biology, vol. 20, No. 23, Dec. 2000, pp. 8933-8943).*
Wilson et al. (Cancer Research, vol. 35, No. 1975, pp. 2954-2958).*
Alonso et al. (Nucleic Acids Research, vol. 15, No. 22, 1987, pp. 9325-9337).*

Amoura et al., "Nucleosome-restricted antibodies are detected before anti-dsDNA and/or antihistone antibodies in serum of MRL-Mp lpr/lpr and +/+ mice, and are present in kidney eluates of lupus mice with proteinuria," *Arthritis & Rheum.* 37:1684-1688 (1994).

Amoura et al., "Presence of antinucleosome autoantibodies in a restricted set of connective tissue diseases," *Arthritis & Rheum.* 43:76-84 (2000).

Chabre et al., "Presence of nucleosome-restricted antibodies in pateints with systemic lupus erythematosus," *Arthritis & Rheumatism* 38:1485-1491 (1995).

Luger et al., "Crystal structure of the nucleosome core particle at 2.8 resolution," *Nature* 3891:251-260 (1997).

Ollier et al., "Autoimmunität," *BIOS Scientific Publishers Limited*, (1994).

Price et al., "Priciples and Practice of Immunoassay," *Macmillan Publishers Ltd*, 2nd Edition (1997).

Rosenberg et al., "Antinuclear antibodies in children with localized scleroderma," *J. Rheum.* 22:2337-2343 (1995).

Subirana, Juan A. "Studies on the thermal denaturation of nucleohistones," *J.Mol.Biol.* 74:363-386 (1973).

Vlachoyiannopoulos et al., "Autoantibodies to HMG-17 nucleosomal protein in patients with scleroderma," *J. Autoimmunity* 7:193-201 (1994).

Yim et al., "The genetics of lupus," *Opin. Neph. and Hypertens.* 10:437-443 (2001).

Bruns et al., "Nucleosomes are major T and B Cell autoantigens in systemic lupus erythematosus," *Arthritis & Rheum.* 43(10):2307-2315 (2000).

Clapier et al., "A critical epitpe for substrate recognition by the nucleosome remodeling ATPase ISWI," *Nuc. Acids Res.*30(3):649-655 (2002).

Jayasena et al., "Nucleosome reconstitution of core-length poly(dG)•poly(dC) and poly(rG-dC) •poly(rG-dC)," *Biochemistry* 28:975-980 (1989).

Dick, T., et al., "Detection of Anti-Nucleosome Antibodies in Patients with SLE or Systemic Sclerosis and Control Panels. Comparison of 4 ELISA Systems," *Kongress der Deutschen Gesselschaft für Rheumatologie*, 30:19-22, Sep. 2001.

(Continued)

*Primary Examiner*—Lisa V Cook
(74) *Attorney, Agent, or Firm*—Seed IP Law Group PLLC (57) ABSTRACT

Compositions and methods are provided for decreasing blood glucose levels in an animal or for preventing or delaying the onset of a rise in blood glucose levels in an animal, comprising administering to the animal an antisense inhibitor of PTP1B expression in combination with at least one glucose-lowering drug. The present invention is also directed to compositions and methods for improving insulin sensitivity in an animal or for preventing or delaying the onset of insulin resistance in an animal. Also provided are compositions and methods for treating or preventing a metabolic condition in an animal. The metabolic condition may be, e.g., diabetes or obesity.

16 Claims, 4 Drawing Sheets

OTHER PUBLICATIONS

Sambrook, J., et al. (eds.), *Molecular Cloning, A Laboratory Manual, Second Edition*, Cold Spring Harbor Laboratory Press, New York, 1989, Chapter 6, "Gel Electrophoresis of DNA," pp. 6.1-6.15.

* cited by examiner

Fig. 1: SDS-PAGE of nucleosomes according to the invention

Fig. 2: TAE agarose gel electrophoresis of the nucleosomes according to the invention.

Fig. 3: Western blot of the nucleosomes according to the invention and histone 1 incubated with α-histone 1-antibody-positive serum Fig. 4: Western blot of the nucleosomes according to the invention and purified Scl-70 incubated with α-Scl-70 antibody-positive serum from a PSS patient.

METHOD FOR PRODUCING A NUCLEOSOME PREPARATION AND USE THEREOF IN IN VITRO DIAGNOSIS OF DISSEMINATED LUPUS ERYTHEMATOSUS (DLE)

The present invention relates to a process for producing a nucleosome preparation which is characterised by being suitable for use in immunofluorescence assays in human samples of specific antibodies directed against the nucleosomes and thus for a diagnosis of systemic lupus erythematosus (SLE), more specific in comparison with the state of the art.

Systemic Lupus Erythematosus (SLE)

Systemic lupus erythematosus (SLE) is a presumably genetically predisposed autoimmune disease from the group of collagenosis [Yim, Y S, Wakeland, E K. The genetics of lupus. Curr. Opi. Nephrol Hypertens, 2001, 10, 437-443]. The disease usually begins between the ages of 25 and 35. Women succumb to the disease much more frequently than men (women:men 9:1, 50 new cases of the disease annually per 100,000 inhabitants) [W. Olliver and D. P. M. Symmons; Autoimmunität, 1995, Spektrum Akademischer Verlag Heidelberg].

SLE is a systemic disease. Most frequently affected are the skin (butterfly erythema), the vessels (Raynoud syndrome), the costal plura (frequently occurring pleuritis) and the joints (arthritis). The serological examination, above all, plays a major part in the diagnosis of SLE.

Serological Detection of SLE

A characteristic feature of SLE is the occurrence of autoreactive antibodies which are aimed against one or several antigens. An example is antibodies to double-stranded DNA (ds-DNA), Sm, SS-A and nucleosomes.

In eukaryotic cells, DNA is organised in chromosomes. When the chromosomes are partially pleated, the structure of the resulting chromatin resembles a chain of beads. The individual beads are referred to as nucleosomes. They consist of nucleic acids and proteins with one protein nucleus containing 8 histone molecules: 2 each of the histones H2A, H2B, H3 and H4. Around this histone centre, the DNA is wound with 146 base pairs. The nucleosomes are linked via the linker DNA (approximately 30-40 Bp,) as a result of which the bead chain-type structure of the chromatin is formed. The histone H1 is situated on the outside of the nucleosomes in the vicinity of the linker DNA [Luger, K, Mader, A W, Richmond, R K, Sargent, D F, Richmond, T J. Crystal structure of the nucleosome core particle at 2.8 Å resolution. Nature, 1997, 389, 251-260].

Chabre et al. was able to show that not only "naked" DNA itself but nucleosomes represent a characteristic autoantigen for SLE [Chabre, H, Amoura, Z, Piette, J C, Godeau, P, Bach, J F, Koutouzov, S. Presence of nucleosome-restricted antibodies in patients with systemic lupus erythematosus. Arthritis Rheum. 1995, 38, 1485-1491]. He provides indications that, during an early stage of SLE, antibodies to nucleosomes are initially formed and antibodies to the components of the nucleosomes (ds-DNA, histones) are detectable in the serum only at a later stage of the disease [Amoura, Z, Chabre, H, Koutouzov, S, Lotton, C, Chabrespines, A, Bach, J F, Jacob, L. Nucleosome-restricted antibodies are detected before anti-ds-DNA and/or antihistone antibodies in serum of MRL-MP lpr/lpr and +/+ Mice, and are present in kidney elutes of lupus mice with proteinuria. Arthritis Rheum. 1994, 37, 1684-1688].

According to the state of the art, antibodies to nucleosomes (ANuA) are described as being sensitive markers for SLE [Chabre et al., 1995, compare above]. In this connection, a process for the production of a nucleosome preparation has been described [Amoura et al., 1994, compare above], in which, following the liberation of the chromatin components from prepared cell nuclei, the nucleosomes are prepared by enzymatic degradation and subjected to purification by saccharose gradient centrifuging. The gradient used was 5 to 20%. So far, however, no working group has succeeded in purifying nucleosomes to such an extent that only SLE patients react.

Studies on the subject of anti-nucleosome antibodies (ANuA) have shown that in 20% to 68% of the patients with progressive system sclerosis (PSS), antibodies to nucleosomes are detectable [Dick, T, Vondegracht, M C, Franz, K, Mierau, R, Genth, E. Nachweis von anti-Nucleosome-Antikörpern bei Patienten mit SLE, systemische Sklerose und Kontrollkollektiven (detection of antinucleosome antibodies in patients with SLE, systemic sclerosis and control collectives). Vergleich von 4 ELISA Systemen (Comparison of 4 ELISA systems), Rheumaklinik und Rheumaforschungsinstitut Aachen; Amoura Z, Koutouzov S, Chabre H, Cacoub P, Amoura I, Musset L, Bach J F, Piette J C. Presence of antinucleosome autoantibodies in a restricted set of connective tissue diseases: antinucleosome antibodies of the IgG3 subclass are markers of renal pathogenicity in systemic lupus erythematosus. Arthritis Rheum. 2000; 43, 76-84]. In the case of polymyositis, too, a small percentage of ANuA are detectable by using the conventional test system. Previously, it has thus not been possible to differentiate between SLE and other diseases by determining the AnuA, as a result of which the value of the ANuA as a diagnostic marker is greatly restricted.

The process for the SLE diagnosis known in the state of the art is consequently non-specific and requires the use of more comprehensive diagnostic methods in order to allow a differentiation between SLE and PSS to be made.

It is consequently the task of the present invention to provide an in vitro diagnosis method by means of which it is possible to specifically detect systemic lupus erythematosus and to differentiate it clearly from progressive system sclerosis.

According to the invention, the task is achieved by a new nucleosome preparation and an assay using these nucleosomes as antigen.

BRIEF SUMMARY OF THE INVENTION

Within the framework of the present invention, it has surprisingly been found that nucleosomes—contrary to the data and information available in the state of the art—are highly suitable as specific markers if they are freed from histone 1, non-histone proteins and the protein Scl-70. These Scl-70 free nucleosomes are obtained by a modified processing method in the case of which, following the purification of the cell nuclei and subsequent nuclease digestion, purified nucleosomes are isolated by density centrifuging with a saccharose gradient. Within the framework of the present invention, it is possible, surprisingly enough, to obtain a fraction which is substantially purer compared with the state of the art than if a saccharose gradient with at least 30 (preferably at least 35) % by weight of saccharose, preferably 30 to 50% by weight, particularly preferably 35 (or 40) to 50 % by weight, most preferably approximately 50% by weight of saccharose is used. In this way, a nucleosome preparation is isolated which consists of mononucleosomes which are free from histone 1 and Scl-70 protein and preferably also free from other non-histone proteins such as e.g. HMGN.

Surprisingly enough, no cross-reactivity with PSS-associated antibodies occurs according to the invention if the nucleosomes are subjected to this modified purification procedure such that the preparation obtained is free from Scl-70-protein.

In the present document, "free from histone 1 and Scl-70 protein" and/or "free from other non-histone proteins" means that the nucleosome preparation does not contain the above-mentioned proteins or only in a low proportion such that it does not interfere with the specific SLE detection and the differentiation of PSS. "Other non-histone proteins" means, for example, also HMG (high mobility group) proteins which have also been described as autoantigens to PSS [Rosenberg A M, Uziel Y, Krafchik B R, Hauta S A, Prokopchuk P A, Silverman E D, Laxer R M. Antinuclear antibodies in children with localized scleroma. J Rheumatol 1995, 22, 2337-2343; Vlachoyiannopoulos P G, Boumba V A, Tzioufas A G, Seferiadis C, Tsolas O, Moutsopoulos H M. Autoantibodies to HMG-17 nucleosomal protein in patients with scleroma. J Autoimmun 1994, 7, 193-201].

Mononucleosomes can be obtained in a pure or almost pure state for the present purposes if nucleosomes are purified e.g. by saccharose gradient centrifuging using a saccharose gradient of more than 30% and separated in this way from histone H1 and other proteins, in particular from a 70 kDa protein fraction. In this way, nucleosomes according to the invention are obtained which, in comparison with the preparations known in the art, have a higher purity level and do not lead to any cross-reactivity with PSS-associated antibodies in ELISA. By using these mononucleosomes in in vitro diagnosis, e.g. as antigen in ELISA, both a sensitive and a highly specific test system is obtained for the serological determination of SLE.

DETAILED DESCRIPTION OF THE INVENTION

The subject matter of the present invention consequently consists of a nucleosome preparation which is free from histone 1 (H1) and Scl-70.

The invention also relates to a method for producing a nucleosome preparation free from histone 1 (H1) and Scl-70 (and preferably free from non-histone protein) in which the cell nucleus is isolated from biological material, the cell nucleus is digested enzymatically with a nuclease and purified by density gradient centrifuging with a saccharose gradient of up to 50% by weight, the nucleosomes being isolated from a fraction with at least 30 (preferably at least 35) % by weight of saccharose, preferably 30 to 50% by weight of saccharose, a range of 35 (or 40) to 50% by weight being particularly preferred. It is most preferable to isolate the nucleosomes from a fraction with approximately 50% by weight of saccharose. As an alternative, a gel filtration can also be carried out. In this case, the fractions containing nucleosomes need to be examined, as described below, as to whether Scl-70, in particular, has been separated off or is still present in the preparation.

The subject matter of the invention also consists of a nucleosome preparation obtainable according to the above-mentioned processes, in particular the above-mentioned process using density gradient centrifuging with a saccharose gradient of at least 30%.

The invention also relates to the use of an above-mentioned nucleosome preparation for the detection of systemic lupus erythematosus (SLE).

According to the invention, an in vitro method is thus provided for the diagnosis of systemic lupus erythematosus (SLE) in the case of which a liquid sample from a patient, such as e.g. serum, is examined by means of an antibody detection method in the case of which the nucleosomes according to the invention are used and SLE is diagnosed by detecting antibodies to the nucleosomes.

This immunological detection is carried out by means of known methods, any desired direct or indirect method being suitable for use for detecting the autoantibodies to nucleosomes according to the invention. In this respect, both liquid phase immunoassays and solid phase immunoassays are conceivable [compare also Price, C. P. and Newman, D. J., compare above Principles and Practice of Immunoassay, $2^{nd}$ Ed., 1997, Stockton Press, New York].

In contrast to the indirect methods, the binding of the antibodies to the antigen is determined in the case of the direct detections by a change in the chemical or physical properties such that subsequent detection steps using labelled SLE binding partners can be omitted.

According to the invention, the detection of the autoantibodies to the nucleosomes preferably takes place in an immunoassay, preferably in a solid phase immunoassay using direct or indirect coupling of a reaction partner with an easily detectable labelling substance. Particularly preferably, the detection can take place in an ELISA, a RIA or a fluorescence immunoassay. The execution of these detection processes is well known to the person skilled in the art.

In an ELISA (enzyme linked immunosorbent assay) according to the present invention, the nucleosomes are bound directly or indirectly to a carrier substance (e.g. polystyrene). Following incubation with the antibodies to be detected, e.g. from the serum of the patient, antigen-bound antibodies are detected by means of substances. These substances can consist of antibodies, fragments of antibodies or highly affine ligands such as e.g. avidin, which binds a biotin label. Suitable enzymes are e.g. peroxidase, alkaline phosphatase, β-galactosidase, urease or glucose oxidase. By adding a chromogenic substance, the bound enzymes and thus the bound nucleosome antibodies, for example, can be quantified.

In a radio immunoassay (RIA), too, the antigen according to the invention, the nucleosomes, is directly or indirectly bound to a carrier substance such as polystyrene. Following incubation with the antibodies to be detected, e.g. from the serum of patients, the antibodies bound to the antigen are detected by means of substances which carry a radioactive label, e.g. $^{125}$I. As in ELISA, these substances can be antibodies, fragments of antibodies or highly affine ligands such as e.g. avidin which binds a biotin label. The quantitative detection of the antibodies bound to the antigen takes place via the bound radioactivity by means of a suitable measuring device.

In the fluorescence immunoassay (FIA) according to the invention, the detection of antibodies to nucleosomes takes place in a manner similar to RIA. The labelling in this test system consists of a fluorescence label such as e.g. fluorescein isothiocyanate (FITC). In this case, too, a quantitative detection of the antibodies bound to the antigen can take place via the detection of the bound fluorescent dye using a suitable measuring device.

Within the framework of the present invention, the detection of antibodies to nucleosomes via an agglutination test or gel diffusion test is also conceivable. In the agglutination test, the particles carrying antigens, e.g. latex or polystyrene beads, are crosslinked by antibodies, e.g. from the serum. The aggregates formed in this way can be detected turbodimetrically.

In the gel diffusion test, adjacent wells in an agar or agarose gel plate are filled with the antigen, e.g. nucleosomes and the antibody, e.g. patient serum. When the substances diffuse from the wells, concentration gradients are formed. In the overlapping areas, highly visible precipitates are formed as soon as the concentration ratios between antigen and antibody reach an optimum and provided that antibodies to the antigen are present in the antibody solution.

According to a preferred embodiment, an in vitro method for SLE diagnosis is provided in the case of which a liquid sample from a patient, such as e.g. patient serum, is examined by means of ELISA, in which the microtitre plates are coated with nucleosomes according to the invention and SLE is diagnosed by detecting antibodies to the nucleosomes in the sample.

According to a particular embodiment of the invention, the microtitre plate is a microtitre plate in which at least some of the cavities (alternatively: all cavities) are coated with the nucleosomes according to the present invention.

Apart from the above-mentioned microtitre plate, the subject matter of the present invention also consists of other fixed carriers which are coated with the nucleosomes according to the invention and/or on whose surface the nucleosomes are fixed (compare above) such as e.g. nitrocellulose or PVDF (polyvinylidene fluoride).

According to a further embodiment, the invention relates to an in vitro process for SLE diagnosis in which a strip test (e.g. EUROLINE®; compare Price, C. P. and Newman, D. J., compare above) is carried out using nucleosome-coated nitrocellulose or PVDA.

Moreover, the invention relates to a kit for carrying out a said in vitro process for the diagnosis of systemic lupus erythematosus which contains an above-mentioned solid carrier, preferably an above-mentioned microtitre plate, nitrocellulose or PVDA. If necessary further reagents and/or auxiliary agents necessary or useful for the execution of the diagnosis and/or detection process may be contained in the kit.

In the following, the invention will be described by way of examples and figures:

EXAMPLE

Isolation of Nucleosomes from Calf Thymus

Conventional Nucleosomes

Extraction of the Calf Thymus 5 g of calf thymus [alternatively, cells from another source can be used, usually of animal tissue (rather less frequently human ones) such as e.g. rat liver, rabbit thymus etc or animal cells such as chicken erythrocytes, and cell cultures (e.g. mouse erythroleukemia L1210 cells)] are absorbed in 150 ml of 0.9% NaCl solution and comminuted. Subsequently, the suspension is homogenised. After filtering off the coarse components, the suspension is centrifuged (15 min at 1,100×g, 4° C.). The pellet is washed twice with 30 ml of 0.9% NaCl solution each and centrifuged as above. Subsequently, the pellet is processed further for nucleus purification.

Nucleus Purification

The nucleus purification takes place according to Subirana [Subirana, J A. Studies on the thermal denaturisation of nucleohistones. J Mol Biol. 1973, 74, 363-86]. The pellet is resuspended in 40 ml of saccharose-1 solution (250 mM saccharose, 3 mM $CaCl_2.2H_2O$) and subsequently centrifuged (12 min, 5,000 rpm and 4° C.). Following the absorption of the pellet in 45 ml of saccharose-2 solution (2M saccharose, 3 mM $CaCl_2.2H_2O$, 0.5% TRITON™-TX-100), centrifuging is repeated (22 min, 13,200×g and 4° C.). The pellet is resuspended in 45 ml of buffer 1 (0.1M Tris/HCl, pH 8.0) and centrifuged once more (15 min, 1,100×g, 4° C.). The last wash step is repeated. The pellet is absorbed in 45 ml of 0.9% NaCl solution and the solution is centrifuged (15 min, 1,100×g, 4° C.). The supernatant liquor is discarded and the pellet containing the cell nucleus is processed further.

Digestion of the Nuclei

The pellet is absorbed in 40 ml of buffer 2 (15 mM Tris/HCl, pH 7.5, 15 mM NaCl, 60 mM $KNO_3$, 0.25 M saccharose, 5 mM $MgCl_2.6H_2O$, 1 mM $CaCl_2.2H_2O$, 1 mM DTT) and the suspension is homogenised. Subsequently, 750 units of the nuclease S7 solution are added to the suspension, the solution is incubated for 30 min in the water bath at 37° C. and subsequently centrifuged (15 min, 4,000 rpm, 4° C.). The pellet formed is absorbed in 10 ml of 2 mM-EDTA solution. The suspension is incubated for 45 min with shaking at room temperature and subsequently centrifuged (15 min, 4,000 rpm, 4° C.). Subsequently, the supernatant solution is carefully removed and used as conventional nucleosome preparation.

Nucleosome Preparation According to the Invention

According to the invention, the nucleosomes are protein depleted, leading essentially to nucleosome nuclei which are used in particular as antigens in in-vitro diagnosis of SLE. In the following, the preparation is described by way of an example.

Nuclease Degradation

The conventional nucleosome preparation is dialysed overnight against buffer 2. Subsequently, the solution is cooled (0° C.) and 5 M NaCl solution is added dropwise with shaking to the nucleosome preparation until an end concentration of 0.55 M NaCl is reached. Subsequently, 150 units of nuclease S7 are added per ml of nucleosome solution, the solution is incubated for 30 min in the water bath at 37° C. and subsequently cooled again to 0° C.

A) Saccharose Gradient (Method 1)

The nucleosomes obtained are purified by density gradient centrifuging: 25 ml of 50%, 30% and 10% saccharose solution each in TE buffer (10 mM Tris, 1 mM EDTA, 0.55 M NaCl) are layered into an ultracentrifuge tube and 5 ml of nucleosome solution placed on top. The gradient is centrifuged overnight at 4° C. and 140,000×g.

Alternatively, other gradients can be used such as e.g. 50/40/30/10% or 50/35/10% etc.

The protein depleted nucleosomes are present in the fraction containing at least 30%, preferably at least 35% (or 40%) and/or approximately 50% saccharose.

B) Gel Filtration (Method 2)

Instead of saccharose density centrifuging, the isolation of the nucleosomes can also take place via gel filtration (HiPrep 26/60 Sephacryl S-300 HR, Amersham-Bioscience). 10 ml of the nucleosomes obtained are applied onto the column equilibrated with TE buffer and eluted with an elution rate of 1 ml/min (TE buffer). The fractions containing nucleosomes are combined.

Characterisation of the Nucleosomes

ELISA Studies: Specificity of Nucleosomes as Autoantigens for SLE

By means of ELISA, studies were carried out with the sera of patients with SLE and progressive system sclerosis, which studies support the theory that the clinical specificity can increase to 100% by using the nucleosomes as autoantigens for SLE. A precondition for this is that the nucleosomes according to the invention can be isolated until no further proteins are detectable by silver staining of the nucleosomes after SDS-PAGE.

Two ELISAs were carried out in which different nucleosome preparations were used for coating of the microtitre plate.

ELISA Coating

The microtitre plates are coated overnight at room temperature with nucleosomes diluted in PBS. Subsequently, the plates coated with antigen are washed with PBS/0.1% TWEEN™ and blocked for 2 hours at room temperature with PBS-10% fetal bovine serum. Subsequently, the microtitre plates are again washed with PBS/0.1% TWEEN™. The incubation of the plates takes place as described in the EUROIMMUN operating instructions.

The two preparations used in ELISA differ from each other by the fact that use was made, on the one hand, of the conventional nucleosome preparation and, on the other hand, of the nucleosome preparation subjected to further purification in order to remover further proteins and to obtain the nucleosomes according to the invention in this way.

TABLE 1

Comparison of the specificity of the nucleosome preparations as autoantigen for disseminated lupus erythematosus *
Autoantibody to nucleosomes

| Antibody to | Disease | Reactive positively |
|---|---|---|
| Conventional nucleosomes | systemic lupus erythematosus | 61% |
|  | Progressive systemic sclerosis | 41% |
|  | Dermatomyositis | 3% |
|  | Healthy blood donor | 0 |
| Nucleosomes according to the invention | systemic lupus erythematosus | 47% |
|  | Progressive systemic sclerosis | 0 |
|  | Dermatomyositis | 0 |
|  | Healthy blood donor | 0 |

* overall, 483 sera were tested including 204 blood donors, 127 LED sera, 119 PSS sera, 33 dermatomyositis sera

SDS-PAGE

Figure 1:
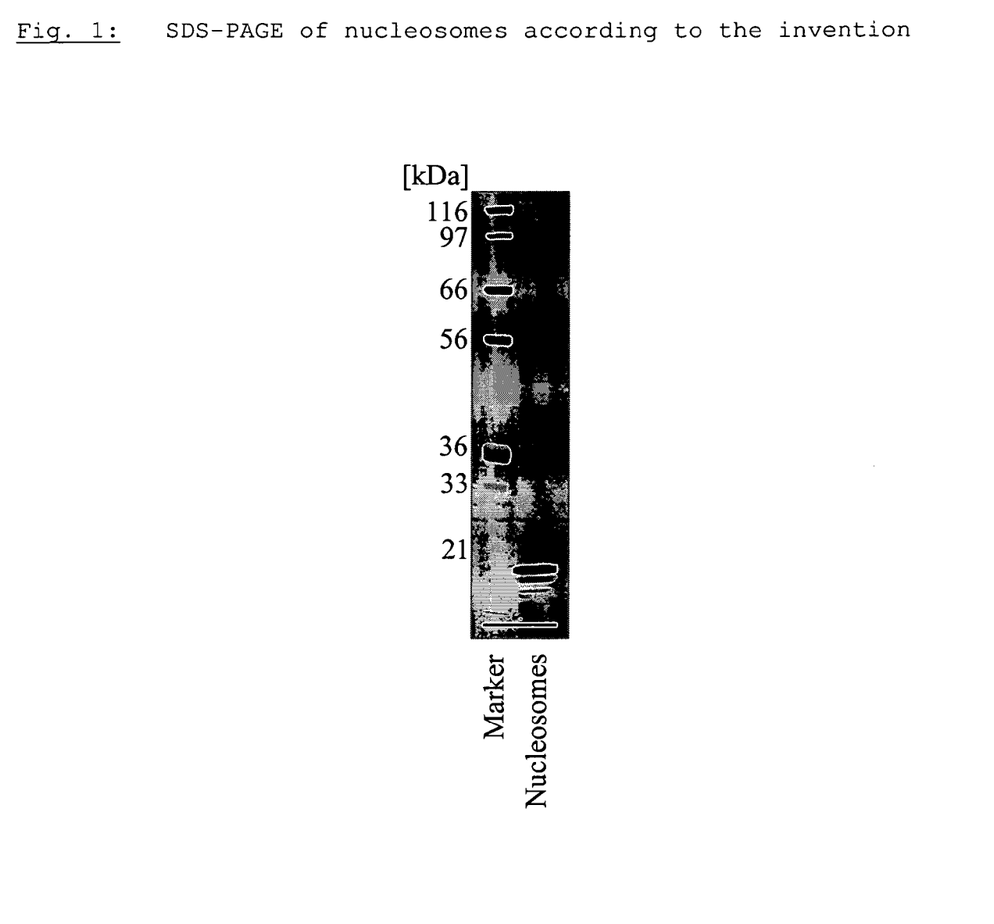
FIG. 1 shows SDS-PAGE of nucleosomes prepared according to a method of the invention.

The nucleosomes according to the invention were examined by means of SDS-PAGE with subsequent silver staining (all materials for the execution of the electrophoresis originate from Invitrogen: NuPAGE 4-12% Bis-Tris gel, NuPage sample buffer, NuPage-MES solvent puffer, Mark-12. Subsequently, silver staining according to Heukeshofen was carried out). The electrophoretic behaviour of the nucleosomes is illustrated in FIG. 1. The SDS-PA gel of the nucleosome preparation according to the invention does not exhibit protein bands above 21 kDa, i.e. no further proteins are detectable in this preparation apart from the histones H2A, H2B, H3 and H4 present in the nucleosome nucleus.

TAE Agarose Gel Electrophoresis

The size of the DNA fragments in the nucleosome preparation was determined by means of native 4% Tris acetate EDTA agarose gel electrophoresis. For the extraction of the proteins, the samples were subjected to Wizard-DNA clean up. The agarose gel of the nucleosomes (FIG. 2.) shows that only mononucleosome DNA with 150 base pairs is present in the nucleosome preparation. Higher chain chromatin residues are not detectable. (Regarding the execution of this electrophoresis method, reference should be made to the following publication: Hans Günter Gassen, Gangolf Schrimpf (Publisher): Gentechnische Methoden, $2^{nd}$ edition, 1999, Spektrum Akademischer Verlag, Heidelberg, Berlin. The staining of the agarose gel takes place by means of ethidium bromide.]

Western Blot

Detection of Histone 1

In contrast to the histones 2A, 2B, 3 and 4, the protein histone 1 is present on the outside of the nucleosomes. The molecular weight of histone 1 is approximately 21 kDa; however, because of its strongly positive charge, this protein exhibits a modified migration behaviour in SDS gel electrophoresis: it appears as a band at approximately 33 kDa.

Histone 1 plays an important part as an autoantigen in rheumatoid arthritis. In order to exclude the possibility of cross-reactions occurring and to obtain the specificity of the nucleosomes for SLE, histone 1 must be separated from the nucleosome preparation. This is possible by the purification methods described above.

Nucleosomes according to the invention were examined regarding their contamination with histone 1 using Western blots. The nucleosomes according to the invention and purified histone 1 were applied to the SDS-PA gel. The gel was blotted onto nitrocellulose and incubated after blotting with α-histone-1 antibody-positive serum. Using this Western blot (FIG. 3) it is possible to show that the nucleosomes according to the invention are free from histone 1.

Detection of Scl-70

Scl-70 is a specific antigen for the diagnosis of progressive system sclerosis (prevalence: 25-70%). This antigen is the protein DNA topoisomerase I. This enzyme participates in the reaction which accompanies a change in the DNA topology. The molecular weight is 100 kDa; however, the antibodies of the PSS sera react also with the 70 kDa degradation product of DNA topoisomerase I, thus also the name Scl-70. As shown in table 1, the ELISA coated with conventional nucleosomes exhibits a sensitivity for PSS of 41%; however, the ELISA coated with nucleosomes according to the invention exhibits no further reaction with the PSS sera. This effect can be attributed to the fact that the Scl-70 was separated off almost quantitatively by the nucleosome preparation according to the invention described above.

By means of Western blots, the nucleosomes according to the invention were examined regarding their contamination with Scl-70. The nucleosomes and isolated Scl-70 were applied to the SDS-PA gel, the proteins were blotted onto nitrocellulose following electrophoresis and incubated with an α-Scl-70 antibody-positive serum. The immunoblot illustrated in FIG. 4 clearly shows that the nucleosomes according to the invention are free from Scl-70.

Summary of the Results:

On the basis of ELISA studies it was found that the nucleosomes according to the invention are specific for SLE.

The preparation of the nucleosomes according to the invention consists only of mononucleosomes, higher chain chromatin residues are not detectable. The investigation of the nucleosomes according to the invention by SDS-PAGE with subsequent silver staining shows only proteins with a molecular weight below 21 kDa. By means of immunoblots it was possible to show that the nucleosomes are free from H1 and Scl-70. Moreover, they preferably contain no other non-histone proteins such as e.g. HMGN.

The invention claimed is:

1. A preparation comprising nucleosomes, wherein said preparation is free from histone 1 and Scl-70 and does not cross react with sera of a patient with progressive systemic sclerosis, and wherein the preparation is obtainable by a process, comprising:
    (a) isolating nuclei from a biological material,
    (b) digesting the nuclei of step (a) with a nuclease to produce nucleosomes,
    (c) purifying the nucleosomes of step (b) by sucrose gradient centrifugation, and
    (d) isolating the nucleosomes from a fraction of step (c) that comprises at least 30% by weight of sucrose.

2. The preparation of claim 1 wherein said nucleosomes are isolated from a fraction comprising at least 40% by weight of sucrose.

3. The preparation of claim 2 wherein said nucleosomes are isolated from a fraction comprising approximately 50% by weight of sucrose.

4. A method for producing a nucleosome preparation that is free from histone 1 and Scl-70 and does not cross react with sera of a patient with progressive systemic sclerosis, comprising:
    (a) isolating nuclei from a biological material,
    (b) digesting the nuclei of step (a) with a nuclease to produce nucleosomes,
    (c) purifying the nucleosomes of step (b) by sucrose gradient centrifugation, and
    (d) isolating the nucleosomes from a fraction of step (c) that comprises at least 30% by weight of sucrose, whereby producing a preparation that comprises nucleosomes, is free from histone 1 and Scl-70, and does not cross react with sera of a patient with progressive systemic sclerosis.

5. The method of claim 4 wherein the nucleosomes are isolated from a fraction comprising at least 40% by weight of sucrose.

6. The method of claim 5 wherein the nucleosomes are isolated from a fraction comprising approximately 50% by weight of sucrose.

7. A method for diagnosing systemic lupus erythematosus (SLE) in a patient, comprising determining the presence or absence of an antibody that binds to the nucleosomes of the preparation of claim 1, wherein the presence of the antibody indicates that the patient has SLE.

8. The method of claim 7, wherein determining the presence or absence of an antibody that binds to the nucleosomes of the preparation is performed via an ELISA comprising a microtitre plate coated with the preparation.

9. The method of claim 7, wherein determining the presence or absence of an antibody that binds to the nucleosomes of the preparation is performed via a strip test comprising a solid carrier coated with the preparation.

10. The method of claim 7, wherein the liquid sample is serum.

11. A solid carrier, wherein the carrier is coated with the preparation according to claim 1.

12. The solid carrier of claim 11 comprising nitrocellulose or polyvinylidene fluoride.

13. The solid carrier of claim 11, wherein the solid carrier is a microtitre plate.

14. A kit comprising a solid carrier according to claim 11.

15. The preparation according to claim 1, wherein the sucrose gradient centrifugation is carried out overnight at 4° C. at 140,000 g.

16. The method of claim 5, wherein the sucrose gradient centrifugation is carried out overnight at 4° C. at 140,000 g.

* * * * *

UNITED STATES PATENT AND TRADEMARK OFFICE
CERTIFICATE OF CORRECTION

PATENT NO. : 7,566,545 B2
APPLICATION NO. : 10/504569
DATED : July 28, 2009
INVENTOR(S) : Waltraud Suer et al.

It is certified that error appears in the above-identified patent and that said Letters Patent is hereby corrected as shown below:

Title page Item (54)

"METHOD FOR PRODUCING A NUCLEOSOME PREPARATION AND USE THEREOF IN IN VITRO DIAGNOSIS OF DISSEMINATED LUPUS ERYTHEMATOSUS (DLE)"

should read:

--METHOD FOR PRODUCING A NUCLEOSOME PREPARATION AND USE THEREOF IN *IN VITRO* DIAGNOSIS OF SYSTEMIC LUPUS ERYTHEMATOSUS (SLE)--.

Title page Item (57)

"Compositions and methods are provided for decreasing blood glucose levels in an animal or for preventing or delaying the onset of a rise in blood glucose levels in an animal, comprising administering to the animal an antisense inhibitor of PTP1B expression in combination with at least one glucose-lowering drug. The present invention is also directed to compositions and methods for improving insulin sensitivity in an animal or for preventing or delaying the onset of insulin resistance in an animal. Also provided are compositions and methods for treating or preventing a metabolic condition in an animal. The metabolic condition may be, e.g., diabetes or obesity."

should read:

--The present invention relates to a process for producing a nucleosome preparation which is characterised by being suitable for use in immunofluorescence assays of specific antibodies directed against the nucleosomes in human samples and thus for a diagnosis of systemic lupus erythematosus (SLE), more specific in comparison with the state of the art.--.

Figures 1-4

Applicants enclosed Sheets 1 through 4, Figures 1-4.

Signed and Sealed this

Third Day of August, 2010

David J. Kappos
*Director of the United States Patent and Trademark Office*

Fig. 1: SDS-PAGE of nucleosomes according to the invention.

Figure 2:
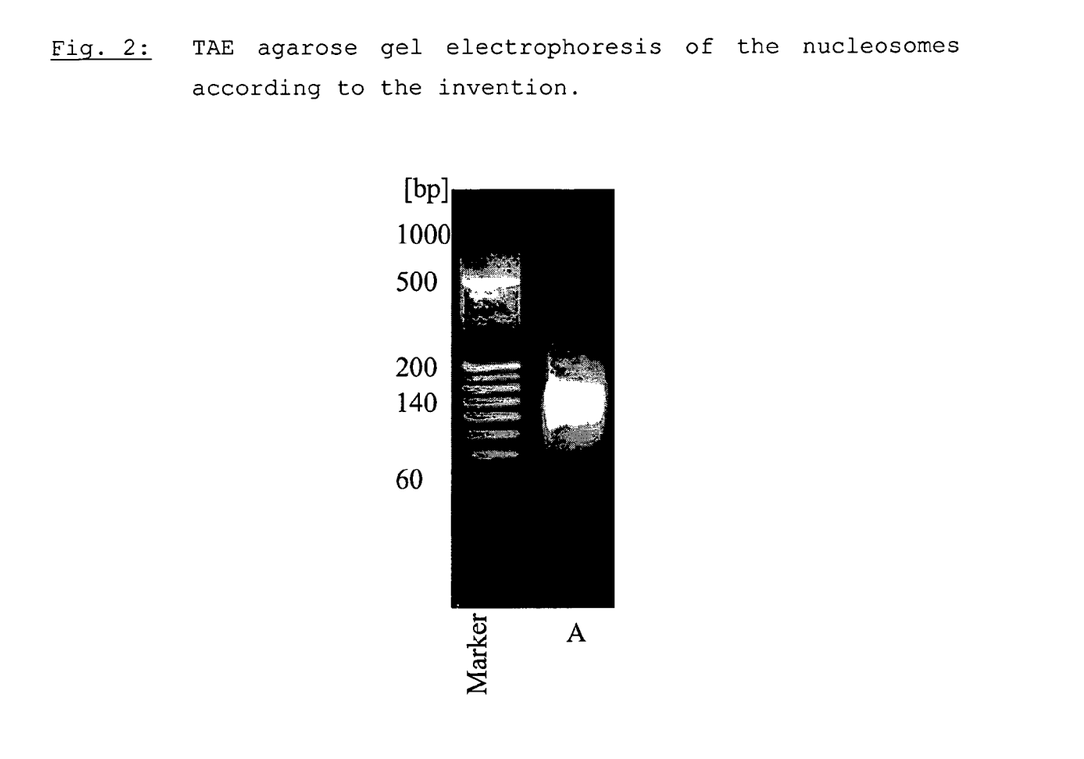
FIG. 2 shows TAE agarose gel electrophoresis of the nucleosomes prepared according to a method of the invention.

Fig. 2: TAE agarose gel electrophoresis of the nucleosomes according to the invention.

Figure 3:
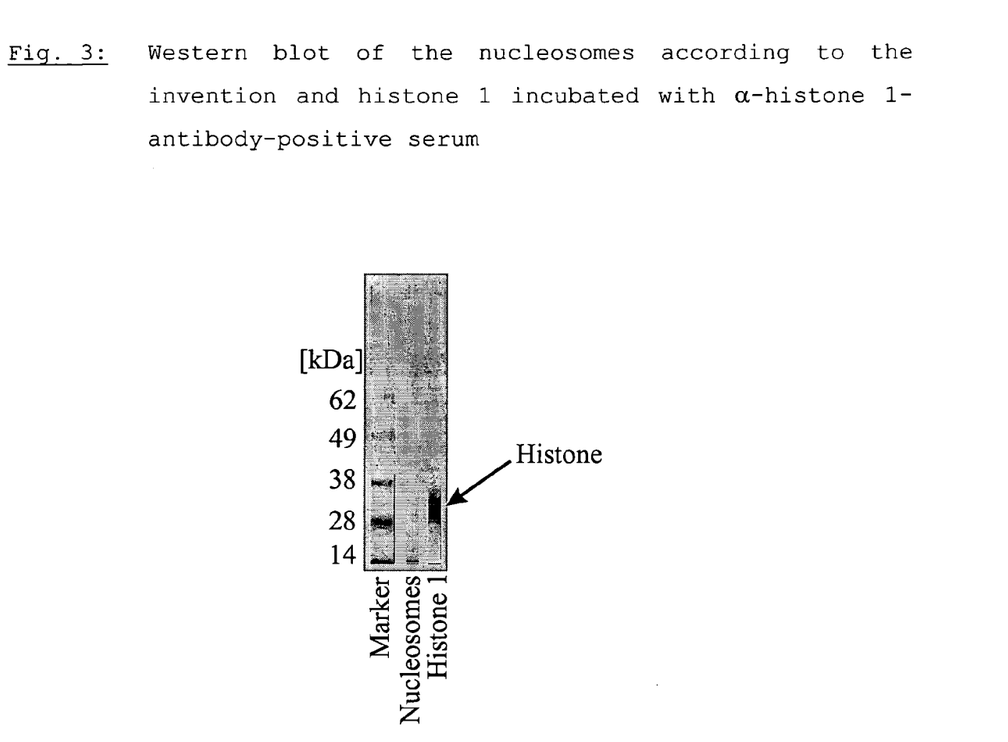
FIG. 3 shows a western blot of the nucleosomes prepared according to a method of the invention and histone 1 incubated with α-histone 1-antibody-positive serum.

Fig. 3: Western blot of the nucleosomes according to the invention and histone 1 incubated with α-histone 1-antibody-positive serum.

Figure 4:
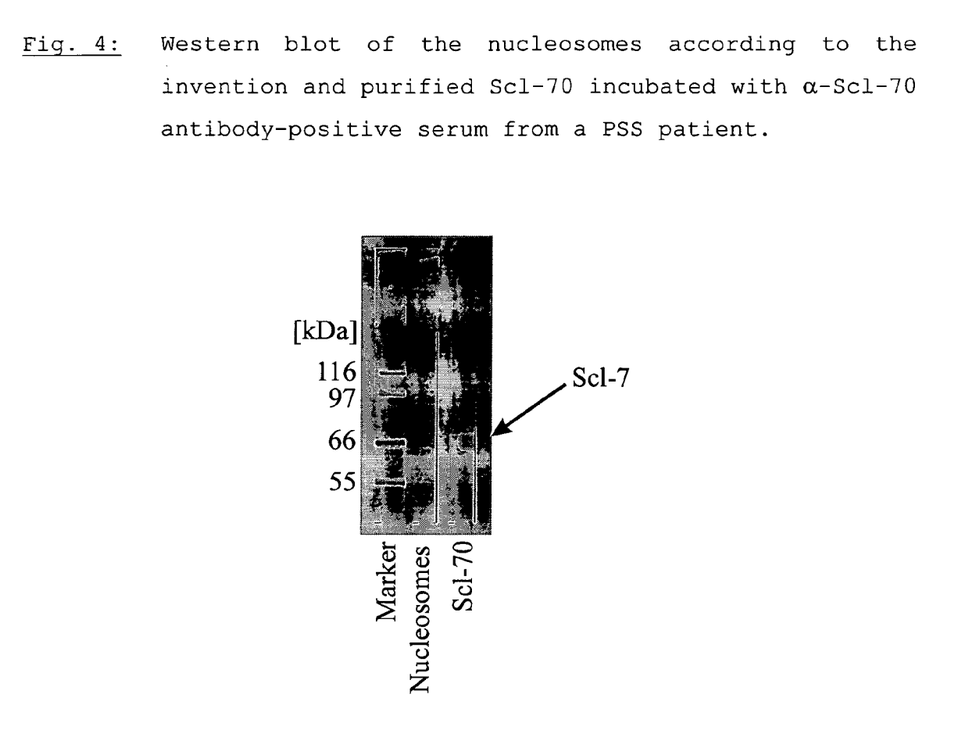
FIG. 4 shows a western blot of the nucleosomes prepared according to a method of the invention and purified Scl-70 incubated with α-Scl-70 antibody-positive serum from a PSS patient.

Fig. 4: Western blot of the nucleosomes according to the invention and purified Scl-70 incubated with α-Scl-70 antibody-positive serum from a PSS patient.

Column 1

Line 1, the section "METHOD FOR PRODUCING A NUCLEOSOME PREPARATION AND USE THEREOF IN IN VITRO DIAGNOSIS OF DISSEMINATED LUPUS ERYTHEMATOSUS (DLE)" is incorrect. A request for title change was filed via Private PAIR on September 24, 2008. The correct title should read --METHOD FOR PRODUCING A NUCLEOSOME PREPARATION AND USE THEREOF IN IN VITRO DIAGNOSIS OF SYSTEMIC LUPUS ERYTHEMATOSUS (SLE)--.

Column 6

Line 15, "TRITON™-TX-100" should read as --TRITON™-X-100--.